(12) United States Patent
Kong et al.

(10) Patent No.: US 11,304,617 B2
(45) Date of Patent: Apr. 19, 2022

(54) DETECTION CIRCUIT, ECG DETECTION APPARATUS, AND WEARABLE DEVICE

(71) Applicant: Shenzhen Goodix Technology Co., Ltd., Shenzhen (CN)

(72) Inventors: Chenyang Kong, Shenzhen (CN); Si Herng Ng, Shenzhen (CN)

(73) Assignee: Shenzhen Goodix Technology Co., Ltd., Shenzhen (CN)

( * ) Notice: Subject to any disclaimer, the term of this patent is extended or adjusted under 35 U.S.C. 154(b) by 0 days.

(21) Appl. No.: 17/139,717

(22) Filed: Dec. 31, 2020

(65) Prior Publication Data

US 2021/0161400 A1 Jun. 3, 2021

Related U.S. Application Data

(63) Continuation of application No. PCT/CN2019/122202, filed on Nov. 29, 2019.

(51) Int. Cl.
*A61B 5/245* (2021.01)
*A61B 5/0245* (2006.01)
(Continued)

(52) U.S. Cl.
CPC ............ *A61B 5/0245* (2013.01); *A61B 5/021* (2013.01); *A61B 5/0205* (2013.01); *A61B 5/28* (2021.01)

(58) Field of Classification Search
CPC ....... A61B 5/0245; A61B 5/28; A61B 5/0205; A61B 5/021
(Continued)

(56) References Cited

U.S. PATENT DOCUMENTS 5,307,817 A * 5/1994 Guggenbuhl ........ A61B 5/0017
600/508
5,382,956 A 1/1995 Baumgartner et al.
(Continued)

FOREIGN PATENT DOCUMENTS

CN 1611185 A 5/2005
CN 103371816 A 10/2013
(Continued)

OTHER PUBLICATIONS

Jing, Zheng, A Simple and Effective Circuit for Detecting Falling off of Leads, Huazhong University of Science and Technology, Jan. 16, 1992, with translation of abstract, 3 pgs.
(Continued)

*Primary Examiner* — Carl H Layno
*Assistant Examiner* — Michael J Lau
(74) *Attorney, Agent, or Firm* — USCH Law, PC

(57) ABSTRACT

Some embodiments of the present disclosure relate to electronic technologies, and provide a detection circuit. According to embodiments of the present disclosure, the detection circuit includes a first load module, a second load module, a third load module, a first detection module, a second detection module, and an obtaining module. A first end of the first detection module is connected to a junction between a first detection electrode and the first load module, a second end of the first detection module is connected to the obtaining module, a first end of the second detection module is connected to a junction between a second detection electrode and the second load module, and a second end of the second detection module is connected to the obtaining module.

19 Claims, 4 Drawing Sheets

(51) Int. Cl.
*A61B 5/28* (2021.01)
*A61B 5/0205* (2006.01)
*A61B 5/021* (2006.01)

(58) Field of Classification Search
USPC .......................................................... 600/509
See application file for complete search history.

(56) References Cited

U.S. PATENT DOCUMENTS

| | | | | |
|---|---|---|---|---|
| 5,788,644 | A * | 8/1998 | Donehoo | A61B 5/304 600/509 |
| 2002/0138011 | A1* | 9/2002 | Rantala | A61B 5/303 600/509 |
| 2003/0083584 | A1 | 5/2003 | Yonce | |
| 2008/0027338 | A1* | 1/2008 | Lu | A61B 5/276 600/509 |
| 2014/0094707 | A1* | 4/2014 | Farringdon | A61B 5/11 600/509 |
| 2015/0042315 | A1* | 2/2015 | Cen | A61B 5/24 324/149 |
| 2015/0241505 | A1 | 8/2015 | Freeman et al. | |
| 2017/0311818 | A1* | 11/2017 | Uutela | A61B 5/11 |
| 2018/0153432 | A1* | 6/2018 | Skrabal | A61B 5/304 |
| 2018/0168458 | A1* | 6/2018 | Pekander | A61B 5/0809 |
| 2018/0184980 | A1* | 7/2018 | Qin | A61B 5/259 |
| 2019/0353692 | A1* | 11/2019 | Batzer | A61B 5/276 |

FOREIGN PATENT DOCUMENTS

| | | |
|---|---|---|
| CN | 107440708 A | 12/2017 |
| CN | 208926356 U | 6/2019 |
| CN | 109975878 A | 7/2019 |
| CN | 110338782 A | 10/2019 |
| CN | 110623661 A | 12/2019 |
| EP | 2443995 A2 | 4/2012 |
| GN | 108663596 A | 10/2018 |
| JP | H 10179531 A | 7/1998 |
| JP | H 11332839 | 12/1999 |

OTHER PUBLICATIONS

Shenzhen Huiding (Goodix) Technology Co., Ltd., First Office Action, CN 201980004368.6, dated Aug. 12, 2020, with translation, 10 pgs.

Shenzhen Goodix Technology Co., International Search Report, PCT/CN2019/122202, dated Nov. 29, 2019, 5 pgs.

Shenzhen Goodix Technology Co., Ltd , Extended European Search Report, EP19934334.4, dated Jun. 9, 2021, 19 pgs.

* cited by examiner

US 11,304,617 B2

DETECTION CIRCUIT, ECG DETECTION APPARATUS, AND WEARABLE DEVICE

CROSS-REFERENCE TO RELATED APPLICATIONS

The present application is a continuation of PCT Patent Application No. PCT/CN2019/122202, entitled "DETECTION CIRCUIT, ECG DETECTION APPARATUS, AND WEARABLE DEVICE", filed on Nov. 29, 2019, which is incorporated herein by reference in its entirety.

TECHNICAL FIELD

The present disclosure relates to electronic technologies, and in particular, to a detection circuit, an electrocardiogram (ECG) detection apparatus, and a wearable device.

BACKGROUND

In a wearable ECG measurement, a left-hand ECG signal and a right-hand ECG signal are collected respectively through a left-hand electrode and through a right-hand electrode, and then are amplified. To improve a reliability of the measurement, wearing detection or falling-off detection needs to be performed on the two electrodes. In addition, during an actual ECG sampling, to reduce an impact of power frequency interference on the measurement, an analog front end (AFE) module usually includes a right leg drive (RLD) circuit to improve the common mode rejection ratio (CMRR) of the AFE. Therefore, three electrodes are needed for ECG sampling, and a right leg electrode is added. The right leg electrode connects RLD circuit output (RLD_OUT) back to the human body and provides a direct current (DC) bias for the ECG input.

The inventor found there are at least the following problem in existing technologies: in actual ECG sampling applications, through conventional wearing detection or falling-off detection, only a wearing state or a falling-off state of a left-hand electrode and a right-hand electrode can be detected, and a wearing state or a falling-off state of a right-leg electrode cannot be determined.

SUMMARY

An objective of some embodiments of the present disclosure is to provide a detection circuit, an ECG detection apparatus and a wearable device, to detect a wearing state or a falling-off state of three detection electrodes.

Embodiments of the present disclosure provide a detection circuit, applicable to an ECG detection apparatus. The ECG detection apparatus includes a first detection electrode, a second detection electrode and a third detection electrode. The detection circuit includes a first load module, a second load module, a third load module, a first detection module, a second detection module and an obtaining module. A first end of the first load module is connected to a first electrical signal, a first end of the second load module is connected to a second electrical signal, a second end of the first load module is configured to connect to the first detection electrode, a second end of the second load module is configured to connect to the second detection electrode, a first end of the third load module is connected to a third electrical signal, and a second end of the third load module is configured to connect to the third detection electrode. An input end of the first detection module is connected to a junction between the first detection electrode and the first load module, and an output end of the first detection module is connected to the obtaining module. An input end of the second detection module is connected to a junction between the second detection electrode and the second load module, and an output end of the second detection module is connected to the obtaining module. Levels of both the first electrical signal and the second electrical signal are opposite to a level of the third electrical signal, and the obtaining module is configured to at least obtain an electrical signal output by the first detection module and an electrical signal output by the second detection module, to determine a wearing state or a falling-off state of the first detection electrode, the second detection electrode and the third detection electrode.

Embodiments of the present disclosure further provide an ECG detection apparatus, including: a first detection electrode, a second detection electrode, a third detection electrode and the detection circuit according to the above embodiment.

Embodiments of the present disclosure further provide a wearable device, including: a first detection electrode, a second detection electrode, a third detection electrode and the detection circuit according to the above embodiment.

Compared with existing technologies, there is an electrical conduction path between the first load module and the third load module, and there is an electrical conduction path between the second load module and the third load module when the three detection electrodes are all worn in the embodiments of the present disclosure. When one or more of the three detection electrodes are not worn, the electrical conduction path is cut off, and electrical signals detected by the first detection module and the second detection module are different from signals detected when the detection electrodes are all worn. Therefore, a wearing state or a falling-off state of the first detection electrode, the second detection electrode and the third detection electrode may be determined according to a signal received by the obtaining module, so that a case in which one or more of the first detection electrode, the second detection electrode and the third detection electrode are not worn normally can be found in time.

In an example, the first detection module includes a first comparator, a first input end of the first comparator serves as an input end of the first detection module, a second input end of the first comparator is connected to a first comparison reference signal, and an output end of the first comparator serves as an output end of the first detection module.

In an example, the second detection module includes a second comparator, a first input end of the second comparator serves as an input end of the second detection module, a second input end of the second comparator is connected to a second comparison reference signal, and an output end of the second comparator serves as an output end of the second detection module.

In an example, the obtaining module is further configured to: determine the wearing state or the falling-off state of the first detection electrode, the second detection electrode and the third detection electrode at least according to a level of the electrical signal output by the first detection module and a level of the electrical signal output by the second detection module.

In an example, a resistance value of the first load module is the same as a resistance value of the second load module. In this example, a design difficulty of other parts of the detection circuit is reduced.

In an example, the detection circuit further includes a third detection module, an input end of the third detection module is connected to a junction between the third detection electrode and the third load module, and an output end of the third detection module is connected to the obtaining module. The obtaining module is configured to obtain the electrical signal output by the first detection module, the electrical signal output by the second detection module, and an electrical signal output by the third detection module, to determine the wearing state or the falling-off state of the first detection electrode, the second detection electrode and the third detection electrode.

In an example, the third detection module includes a third comparator, a first input end of the third comparator serves as an input end of the third detection module, a second input end of the third comparator is connected to a third comparison reference signal, and an output end of the third comparator serves as an output end of the third detection module.

In an example, each of the first load module, the second load module, and the third load module includes: a first resistor unit or a first current source.

In an example, each of the first load module, the second load module, and the third load module includes: a second resistor unit and a first change-over switch, a first fixed end of the first change-over switch serves as a first end of a load module corresponding to the first change-over switch, a second fixed end of the first change-over switch serves as a third end of the load module corresponding to the first change-over switch, a movable end of the first change-over switch is connected to a first end of the second resistor unit, and a second end of the second resistor unit serves as a second end of the load module corresponding to the first change-over switch. Or, each of the first load module, the second load module, and the third load module includes: a second current source, a third current source and a first change-over switch, a movable end of the first change-over switch serves as a second end of a load module corresponding to the first change-over switch, a first fixed end of the first change-over switch is connected to an end of the second current source, the other end of the second current source serves as a first end of the load module corresponding to the first change-over switch, a second fixed end of the first change-over switch is connected to an end of the third current source, and the other end of the third current source serves as a third end of the load module corresponding to the first change-over switch, where the first electrical signal and the second electrical signal are high-level signals, and the third electrical signal is a low-level signal; and both a third end of the first load module and a third end of the second load module are connected to a low-level signal, and a third end of the third load module is connected to a high-level signal.

In an example, the obtaining module is further configured to: control, after determining that the ECG detection apparatus is in a direct current (DC) working mode, the movable end of the first change-over switch to connect to the first fixed end of the first change-over switch; and control, after determining that the ECG detection apparatus is in an alternating current (AC) working mode, the movable end of the first change-over switch to periodically switch between being connected to the first fixed end of the first change-over switch and connected to the second fixed end of the first change-over switch.

In an example, the detection circuit further includes a first logic processing module and a second logic processing module, the output end of the first detection module is connected to the obtaining module through the first logic processing module, and the output end of the second detection module is connected to the obtaining module through the second logic processing module. The first logic processing module is configured to output an electrical signal with a first level when an electrical signal output by the first detection module meets a preset first sequential logic, and output an electrical signal with a second level when an electrical signal output by the first detection module does not meet the preset first sequential logic, the first level being opposite to the second level. And the second logic processing module is configured to output an electrical signal with a third level when an electrical signal output by the second detection module meets a preset second sequential logic, and output an electrical signal with a fourth level when an electrical signal output by the second detection module does not meet the preset second sequential logic, the third level being opposite to the fourth level. In this example, a logic processing module is added to the detection circuit, which can lower requirements for a processing capability of the obtaining module, to make types of the obtaining module that can be selected various.

In an example, the detection circuit further includes a first switch, a second switch and a third switch, the second end of the first load module is connected to the first detection electrode through the first switch, the second end of the second load module is connected to the second detection electrode through the second switch, and the second end of the third load module is connected to the third detection electrode through the third switch.

In an example, the detection circuit further includes a fourth load module, a fifth load module, a sixth load module, a fourth detection module and a fifth detection module, a first end of the fourth load module is connected to a fourth electrical signal, a second end of the fourth load module is configured to connect to the first detection electrode, a first end of the fifth load module is connected to a fifth electrical signal, a second end of the fifth load module is configured to connect to the second detection electrode, a first end of the sixth load module is connected to a sixth electrical signal, and a second end of the sixth load module is configured to connect to the third detection electrode. An input end of the fourth detection module is connected to a junction between the fourth load module and the first detection electrode, an output end of the fourth detection module is connected to the obtaining module, an input end of the fifth detection module is connected to a junction between the fifth load module and the second detection electrode, and an output end of the fifth detection module is connected to the obtaining module. Levels of both the fourth electrical signal and the fifth electrical signal are opposite to a level of the sixth electrical signal, each of the first load module, the second load module, and the third load module includes the first resistor unit, and each of the fourth load module, the fifth load module and the sixth load module includes: a fourth current source and a fourth switch, where a first end of the fourth current source serves as a first end of a load module corresponding to the fourth current source, a second end of the fourth current source is connected to a first end of the fourth switch, and a second end of the fourth switch serves as a second end of the load module corresponding to the fourth current source. Or, each of the first load module, the second load module, and the third load module includes: the second resistor unit and the first change-over switch, and each of the fourth load module, the fifth load module and the sixth load module includes: a fifth current source, a sixth current source, a second change-over switch and a fourth switch, where a movable end of the second change-over switch is connected to a first end of the fourth switch, a second end of the fourth switch serves as a second end of a load module corresponding to the second change-over switch, a first fixed end of the second change-over switch is connected to an end of the fifth current source, the other end of the fifth current source serves as a first end of the load module corresponding to the second change-over switch, a second fixed end of the second change-over switch is connected to an end of the sixth current source, and the other end of the sixth current source serves as a third end of the load module corresponding to the second change-over switch. The fourth electrical signal and the fifth electrical signal are high-level signals, and the sixth electrical signal is a low-level signal. Both a third end of the fourth load module and a third end of the fifth load module are connected to a low-level signal, and a third end of the sixth load module is connected to a high-level signal. And the obtaining module is further configured to: turn on, after determining that the ECG detection apparatus is in a sleep state, the first switch, the second switch, and the third switch, turn off the fourth switch in the fourth load module, the fifth load module, and the sixth load module, and obtain the electrical signal output by the first detection module and the electrical signal output by the second detection module to determine whether the first detection electrode, the second detection electrode, and the third detection electrode are worn; and turn off, after determining that the ECG detection apparatus is in a working state, the first switch, the second switch, and the third switch, turn on the fourth switch in the fourth load module, the fifth load module, and the sixth load module, and obtain an electrical signal output by the fourth detection module and an electrical signal output by the fifth detection module to determine whether the first detection electrode, the second detection electrode, and the third detection electrode fall off.

BRIEF DESCRIPTION OF THE DRAWINGS

One or more embodiments are described by way of examples with reference to the corresponding figures in the accompanying drawings, and the descriptions are not to be construed as limiting the embodiments. Elements in the accompanying drawings that have the same reference numerals are represented as similar elements, and unless otherwise particularly stated, the figures in the accompanying drawings are limited to a scale. A division of the following embodiments is for convenience of description, and should not constitute any limitation to specific implementations of the present disclosure, and various embodiments may be combined and referenced with each other without contradiction.

DETAILED DESCRIPTION

To make objectives, technical solutions, and advantages of the present disclosure clearer, some embodiments of the present disclosure are described in detail with reference to the accompanying drawings and embodiments hereinafter. It should be understood that the specific embodiments described herein are merely used to explain the present disclosure rather than limit the present disclosure.

Figure 1:
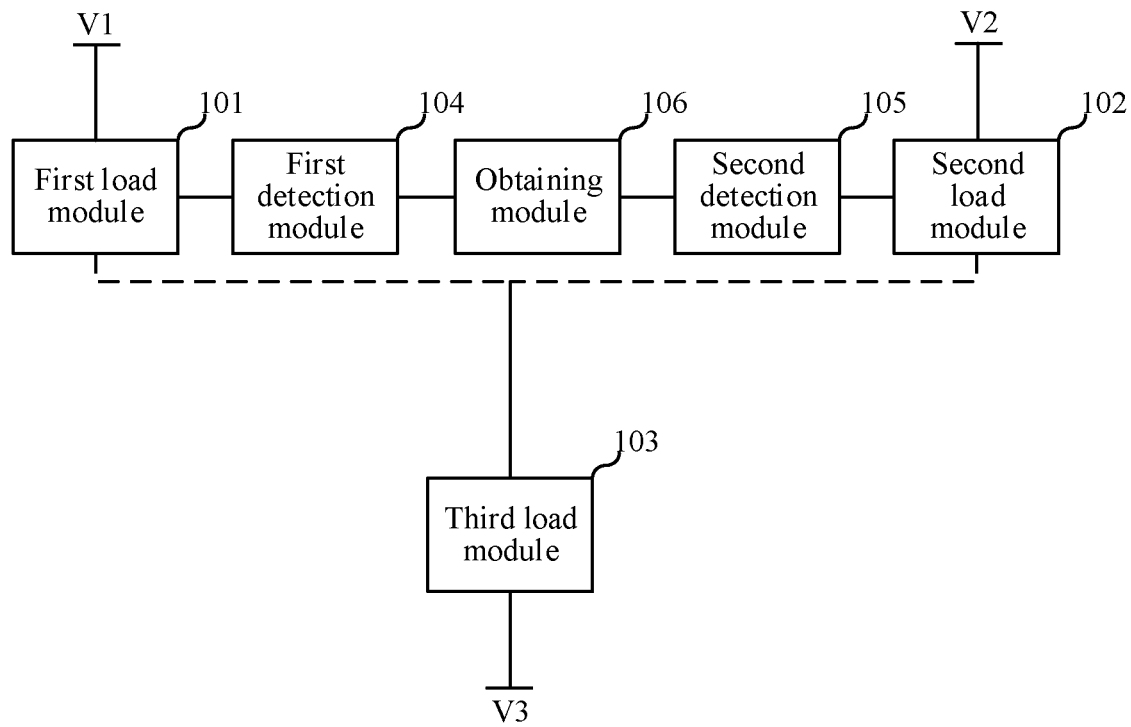
FIG. 1 is a schematic structural diagram of a detection circuit according to a first embodiment of the present disclosure.

A first embodiment of the present disclosure relates to a detection circuit, applied to an ECG detection apparatus, where the ECG detection apparatus includes a first detection electrode, a second detection electrode and a third detection electrode. As shown in FIG. 1, the detection circuit includes a first load module 101, a second load module 102, a third load module 103, a first detection module 104, a second detection module 105, and an obtaining module 106. A first end of the first load module 101 is connected to a first electrical signal (V1), a first end of the second load module 102 is connected to a second electrical signal (V2), a second end of the first load module 101 is configured to connect to the first detection electrode, a second end of the second load module 102 is configured to connect to the second detection electrode, a first end of the third load module 103 is connected to a third electrical signal (V3), and a second end of the third load module 103 is configured to connect to the third detection electrode. An input end of the first detection module 104 is connected to a junction between the first detection electrode and the first load module 101, and an output end of the first detection module 104 is connected to the obtaining module 106. An input end of the second detection module 105 is connected to a junction between the second detection electrode and the second load module 102, and an output end of the second detection module 105 is connected to the obtaining module 106. Levels of both the first electrical signal and the second electrical signal are opposite to a level of the third electrical signal. The obtaining module 106 is configured to at least obtain an electrical signal output by the first detection module and an electrical signal output by the second detection module, to determine a wearing state or a falling-off state of the first detection electrode, the second detection electrode and the third detection electrode.

In this embodiment, determining the wearing state or the falling-off state of the first detection electrode, the second detection electrode, and the third detection electrode is: determining whether the first detection electrode, the second detection electrode, and the third detection electrode are worn, or determining whether the first detection electrode, the second detection electrode and the third detection electrode fall off after being worn.

Specifically, when any two of the first detection electrode, the second detection electrode, and the third detection electrode are worn, there is an electrical connection between the worn electrodes. When the first detection electrode, the second detection electrode, and the third detection electrode are all worn or do not fall off after being worn, there is an electrical conduction path between the first load module 101 and the third load module 103, and there is an electrical conduction path between the second load module 102 and the third load module 103. When the first detection electrode is not worn or fall off after being worn, and the second detection electrode and the third detection electrode are worn or do not fall off after being worn, there is no electrical conduction path between the first load module 101 and the third load module 103, and a voltage at the junction between the first detection electrode and the first load module 101 changes and is pulled up to a voltage value of the first electrical signal. When the second detection electrode is not worn or fall off after being worn, and the first detection electrode and the third detection electrode are worn or do not fall off after being worn, there is no electrical conduction path between the second load module 102 and the third load module 103, and a voltage at the junction between the second detection electrode and the second load module 102 changes and is pulled up to a voltage value of the second electrical signal. When the third detection electrode is not worn or fall off after being worn, or any two of the first detection electrode, the second detection electrode, and the third detection electrode are not worn or fall off after being worn, there is no electrical conduction path between the first load module 101 and the third load module 103, and there is no electrical conduction path between the second load module 102 and the third load module 103. A voltage at the junction between the first detection electrode and the first load module 101 changes and is pulled up to a voltage value of the first electrical signal, and the voltage at the junction between the second detection electrode and the second load module 102 changes and is pulled up to a voltage value of the second electrical signal. It can be learned from the above that through the detection circuit mentioned in this embodiment, electrical signals detected by the detection modules when any one of the first detection electrode, the second detection electrode, and the third detection electrode is not worn or falls off are different from electrical signals detected when the three detection electrodes are all worn. Therefore, the detection circuit can detect whether the first detection electrode, the second detection electrode, and the third detection electrode are worn or whether the first detection electrode, the second detection electrode, and the third detection electrode fall off after being worn.

In an example, the first electrical signal and the second electrical signal are high-level signals. For example, the first electrical signal and the second electrical signal are signals at an output end of a first power supply. The third electrical signal is a low-level signal. For example, the third electrical signal is a signal connected to ground.

In an example, the first detection module 104 includes a first comparator, a first input end of the first comparator serves as the input end of the first detection module 104, a second input end of the first comparator is connected to a first comparison reference signal, and an output end of the first comparator serves as the output end of the first detection module 104.

In an example, the second detection module 105 includes a second comparator, a first input end of the second comparator serves as the input end of the second detection module 105, a second input end of the second comparator is connected to a second comparison reference signal, and an output end of the second comparator serves as the output end of the second detection module 105.

In an example, when a resistance value of the first load module and a resistance value of the second load module are the same, the first comparison reference signal and the second comparison reference signal may be the same signal.

It is worth mentioning that the comparator compares a signal detected by the detection module with a comparison reference signal, and outputs a high level or a low level according to a comparison result, so that a user or the obtaining module 106 can determine, according to the high level or the low level output by the comparator, a wearing state or a falling-off state of the first detection electrode, the second detection electrode and the third detection electrode, thereby reducing a difficulty of determining and improving an accuracy of the wearing detection or the falling-off detection on the first detection electrode, the second detection electrode and the third detection electrode.

It should be noted that a person skilled in the art can understand that in an actual application, other devices or other circuit forms may be selected as the first detection module 104 and the second detection module 105. Specific circuits of the first detection module and the second detection module are not limited in this embodiment.

In an example, a resistance value of the first load module 101 is the same as a resistance value of the second load module 102.

It is worth mentioning that because the resistance value of the first load module 101 is the same as the resistance value of the second load module 102, analysis of an equivalent circuit of the detection circuit is easier, thereby reducing a design difficulty of other parts of the detection circuit.

It should be noted that a person skilled in the art can understand that in an actual application, a voltage of the first comparison reference signal and a voltage of the second comparison reference signal are determined according to resistance values of the first load module 101, the second load module 102, and the third load module 103. A voltage value of the first comparison reference signal and a voltage value of the second comparison reference signal may be the same or different.

In an example, the detection circuit further includes a first switch, a second switch and a third switch, the second end of the first load module 101 is connected to the first detection electrode through the first switch, the second end of the second load module 102 is connected to the second detection electrode through the second switch, and the second end of the third load module 103 is connected to the third detection electrode through the third switch.

It is worth mentioning that each load module is connected to a detection electrode through a switch, and the detection circuit may be disconnected when wearing detection is not required, thereby reducing a power consumption of the detection circuit.

Device types of the obtaining module 106 are described below by using examples.

In an example, the obtaining module 106 is a device with a determining function. Specifically, the obtaining module 106 determines the wearing state or the falling-off state of the first detection electrode, the second detection electrode and the third detection electrode at least according to a level of the electrical signal output by the first detection module and a level of the electrical signal output by the second detection module. For example, the obtaining module 106 is a central processing unit (CPU). The obtaining module 106 determines a wearing state or a falling-off state of the first detection electrode, the second detection electrode, and the third detection electrode at least according to a level of an electrical signal output by the first detection module, a level of an electrical signal output by the second detection module, and a pre-stored constraint relationship between levels of both an electrical signal output by the first detection module and an electrical signal output by the second detection module and a wearing state or a falling-off state of the detection electrode.

In another example, the obtaining module 106 is a display module. For example, the obtaining module 106 is a display, configured to at least display an electrical signal output by the first detection module and an electrical signal output by the second detection module, so that a user can determine a wearing state or a falling-off state of the first detection electrode, the second detection electrode and the third detection electrode according to display of the display. In another example, the obtaining module 106 includes a first indicator light and a second indicator light. The first indicator light is connected to the first detection module 104, and the second indicator light is connected to the second detection module 105. The user determines a wearing state or a falling-off state of the first detection electrode, the second detection electrode and the third detection electrode according to an on-state or an-off state of the first indicator light and the second indicator light.

It should be noted that a person skilled in the art can understand that in an actual application, the obtaining module may alternatively be another device, and a specific type of the obtaining module is not limited in this embodiment.

Circuit structures of the first load module 101, the second load module 102, and the third load module 103 are described below by using examples.

In a first example, each of the first load module 101, the second load module 102, and the third load module 103 includes: a first resistor unit or a first current source.

In a second example, each of the first load module 101, the second load module 102, and the third load module 103 includes: a second resistor unit and a first change-over switch, a first fixed end of the first change-over switch serves as a first end of a load module corresponding to the first change-over switch, a second fixed end of the first change-over switch serves as a third end of the load module corresponding to the first change-over switch, a movable end of the first change-over switch is connected to a first end of the second resistor unit, and a second end of the second resistor unit serves as a second end of the load module corresponding to the first change-over switch. The first electrical signal and the second electrical signal are high-level signals, and the third electrical signal is a low-level signal. Both a third end of the first load module 101 and a third end of the second load module 102 are connected to a low-level signal, and a third end of the third load module 103 is connected to a high-level signal.

In a third example, each of the first load module 101, the second load module 102, and the third load module 103 includes: a second current source, a third current source and a first change-over switch, a movable end of the first change-over switch serves as a second end of a load module corresponding to the first change-over switch, a first fixed end of the first change-over switch is connected to an end of the second current source, the other end of the second current source serves as a first end of the load module corresponding to the first change-over switch, a second fixed end of the first change-over switch is connected to an end of the third current source, and the other end of the third current source serves as a third end of the load module corresponding to the first change-over switch. The first electrical signal and the second electrical signal are high-level signals, and the third electrical signal is a low-level signal. Both a third end of the first load module 101 and a third end of the second load module 102 are connected to a low-level signal, and a third end of the third load module 103 is connected to a high-level signal.

Optionally, the first change-over switch is a single pole double throw switch.

In an example, with respect to the detection circuit corresponding to the above second example and the above third example, the obtaining module 106 is further configured to: control, after determining that the ECG detection apparatus is in a DC working mode, the movable end of the first change-over switch to connect to the first fixed end of the first change-over switch; and control, after determining that the ECG detection apparatus is in an AC working mode, the movable end of the first change-over switch to periodically switch between being connected to the first fixed end of the first change-over switch and connected to the second fixed end of the first change-over switch. For example, a switching period of the movable end of the first change-over switch is ½ of a control period. The movable end of the first change-over switch is connected to the first fixed end of the first change-over switch in a first half of the control period, and to the second fixed end of the first change-over switch in a second half of the control period. Alternatively, the movable end of the first change-over switch is connected to the second fixed end of the first change-over switch in the first half of the control period, and to the first fixed end of the first change-over switch in the second half of the control period.

It is worth mentioning that the detection circuit may switch detection modes according to the working mode of the ECG detection apparatus, so that the detection circuit is applicable to a DC coupling scenario and an AC coupling scenario.

Optionally, when the first load module 101, the second load module 102, and the third load module 103 adopt the structures shown in the second example and the third example, the detection circuit further includes a first logic processing module and a second logic processing module. The output end of the first detection module 104 is connected to the obtaining module 106 through the first logic processing module, and the output end of the second detection module 105 is connected to the obtaining module 106 through the second logic processing module. The first logic processing module is configured to output an electrical signal with a first level when an electrical signal output by the first detection module 105 meets a preset first sequential logic, and output an electrical signal with a second level when an electrical signal output by the first detection module 105 does not meet the preset first sequential logic, the first level being opposite to the second level. The second logic processing module is configured to output an electrical signal with a third level when an electrical signal output by the second detection module 106 meets preset a second sequential logic, and output an electrical signal with a fourth level when an electrical signal output by the second detection module 106 does not meet the preset second sequential logic, the third level being opposite to the fourth level.

It is worth mentioning that a logic processing module is added to the detection circuit, which can lower requirements for a processing capability of the obtaining module, to make types of the obtaining module that can be selected various.

Value ranges of the first comparison reference signal and the second comparison reference signal are described below by using examples with reference to the circuit form of the detection circuit.

In an example, the first load module 101, the second load module 102, and the third load module 103 have a structure shown in the above first example. The first electrical signal and the second electrical signal are high-level signals, the third electrical signal is a low-level signal, a resistance value of the first load module 101 is the same as a resistance value of the second load module 102, and a resistance value of the third load module 103 is equal to ½ of the resistance value of the first load module 101. In this case, voltage values of the first comparison reference signal and the second comparison reference signal are greater than ½ of a voltage value of the high-level signal and less than the voltage value of the high-level signal.

In another example, the first load module 101, the second load module 102, and the third load module 103 have a structure shown in the above second example. A resistance value of the first load module 101 is the same as a resistance value of the second load module 102, and a resistance value of the third load module 103 is equal to ½ of the resistance value of the first load module 101. In this case, voltage values of the first comparison reference signal and the second comparison reference signal are greater than ⅔ of a voltage value of the high-level signal and less than the voltage value of the high-level signal.

In still another example, the first load module 101, the second load module 102, and the third load module 103 have a structure shown in the above third example. Currents output by the second current source and the third current source in each of the first load module 101, the second load module 102 and the third load module 103 are the same. In this case, voltage values of the first comparison reference signal and the second comparison reference signal are greater than ⅔ of a voltage value of the high-level signal and less than the voltage value of the high-level signal.

The circuit form of the detection circuit is described below by using examples for the structure types of the first load module, the second load module and the third load module mentioned in the above examples.

Assuming that the first detection electrode is a left-hand electrode, including a first polarizing voltage (VC1), a first polarizing resistance (Re1) and a first polarizing capacitance (Ce1), the second detection electrode is a right-hand electrode, including a second polarizing voltage (VC2), a second polarizing resistance (Re2), and a second polarizing capacitance (Ce2), and the third detection electrode is an RLD electrode, including a third polarizing voltage (VC3), a third polarizing resistance (Re3) and the third polarization capacitance (Ce3). The first end of the comparator serves as the input end of the detection module, and the second end of the comparator is the input end of the comparison reference signal.

Figure 2:
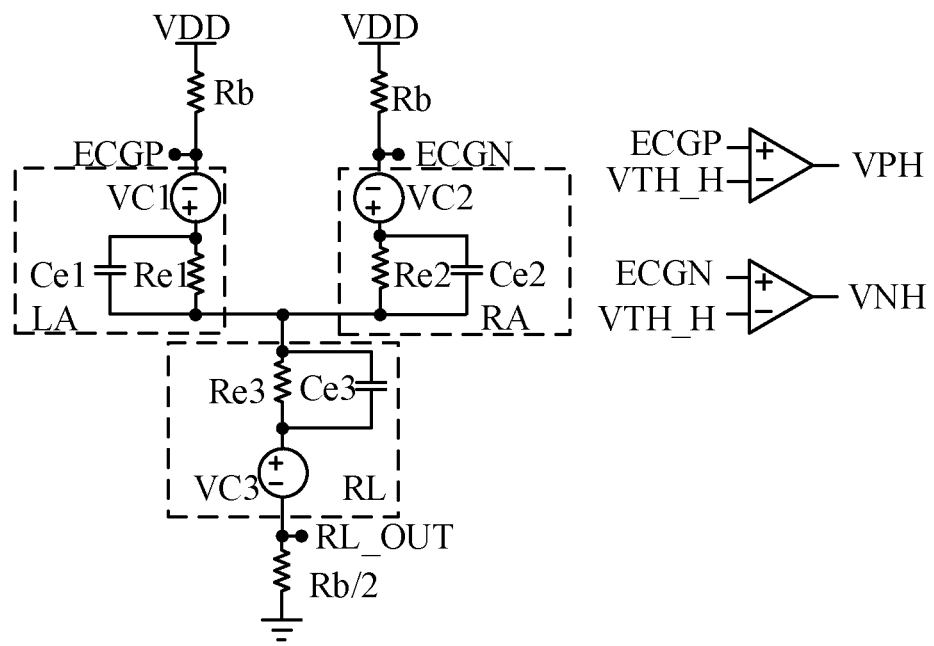
FIG. 2 is a schematic diagram of a circuit connection between a detection circuit and an ECG detection apparatus in an example A according to the first embodiment of the present disclosure.

In an example A, each of the first load module 101, the second load module 102, and the third load module 103 includes a first resistor unit. The first electrical signal and the second electrical signal are high-level signals with a voltage value of VDD, and the third electrical signal is a low-level signal. A resistance value of the first resistor units in the first load module 101 and the second load module 102 is Rb, and a resistance value of the first resistor unit in the third load module 103 is Rb/2. Assuming that the first comparison reference signal and the second comparison reference signal are the same and both are VTH_H, where VDD/2<VTH_H<VDD. When the first detection electrode, the second detection electrode and the third detection electrode are all worn, a schematic circuit diagram of the detection circuit and the ECG detection apparatus is shown in FIG. 2 if human body resistance ignored. In FIG. 2, LA represents the left-hand electrode, RA represents the right-hand electrode, RL represents the RLD electrode, ECGP represents a junction between the first detection electrode and the first load module 101, ECGN represents a junction between the second detection electrode and the second load module 102, and RL_OUT represents a junction between the third detection electrode and the third load module 103. A correspondence between a wearing state of the detection electrode and an output of the comparator is shown in Table 1. When LA, RA, and RL are all worn, due to of Rb being much greater than Re1, Re2, and Re3, voltages of ECGP and ECGN are about VDD/2 if a polarizing voltage is relatively small, where VTH_H>VDD/2, an output of the first comparator (hereinafter referred to as VPH) and an output of the second comparator (hereinafter referred to as VNH) are both low levels. When LA is not worn, and RA and RL are worn, the voltage of ECGP is pulled up to VDD, the voltage of ECGN is about VDD/3 after the voltage VDD is divided, and therefore, VPH is a high level, and VNH is a low level. When RA is not worn, and LA and RL are worn, similar to the case in which LA is not worn, VPH is a low level, and VNH is a high level. When RL is not worn, or any two of LA, RA and RL are not worn, voltages of ECGP and ECGN are both pulled up to VDD, and VPH and VNH are both high levels.

TABLE 1

| State | VPH | VNH |
| --- | --- | --- |
| RL is not worn, or any two of LA, RA and RL are not worn | High level | High level |
| LA is not worn | High level | Low level |
| RA is not worn | Low level | High level |
| All are worn | Low level | Low level |

Figure 3:
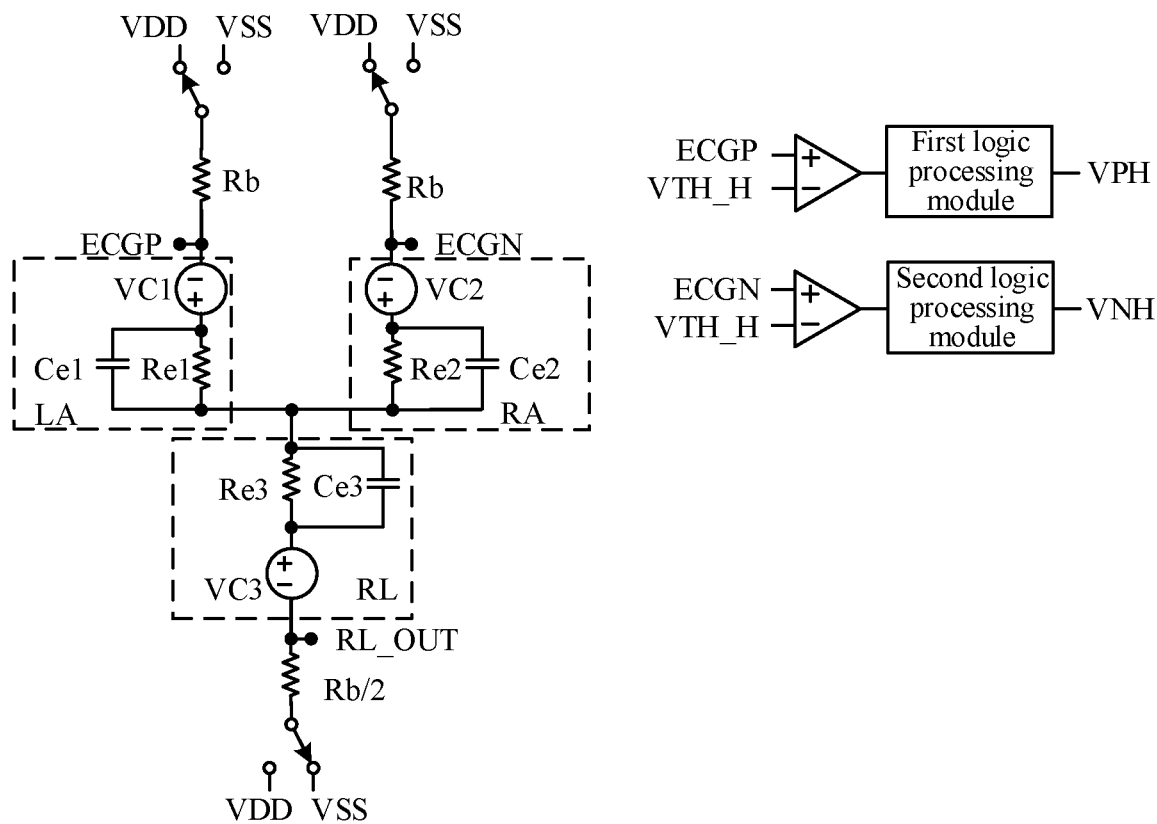
FIG. 3 is a schematic diagram of a circuit connection between a detection circuit and an ECG detection apparatus in an example B according to the first embodiment of the present disclosure.
Figure 4:
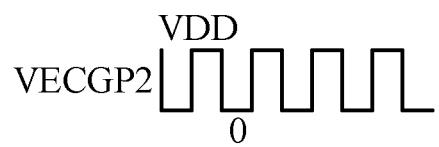
FIG. 4 is a waveform diagram of ECGP according to the first embodiment of the present disclosure.

In an example B, each of the first load module 101, the second load module 102, and the third load module 103 includes: a second resistor unit and a first change-over switch, a first fixed end of the first change-over switch serves as a first end of a load module corresponding to the first change-over switch, a second fixed end of the first change-over switch serves as a third end of the load module corresponding to the first change-over switch, a movable end of the first change-over switch is connected to a first end of the second resistor unit, and a second end of the second resistor unit serves as a second end of the load module corresponding to the first change-over switch. The first electrical signal and the second electrical signal are high-level signals, and the third electrical signal is a low-level signal. Both a third end of the first load module 101 and a third end of the second load module 102 are connected to a low-level signal, and a third end of the third load module 103 is connected to a high-level signal. A voltage value of the high-level signal is VDD. A resistance value of the second resistor units in the first load module 101 and the second load module 102 is Rb, and a resistance value of the second resistor unit in the third load module 103 is Rb/2. Assuming that the first comparison reference signal and the second comparison reference signal are the same and both are VTH_H, where 2VDD/3<VTH_H<VDD. When the first detection electrode, the second detection electrode and the third detection electrode are all worn, a schematic circuit diagram of the detection circuit and the ECG detection apparatus is shown in FIG. 3 if a human body resistance is ignored. In FIG. 3, LA represents the left-hand electrode, RA represents the right-hand electrode, RL represents the RLD electrode, ECGP represents a junction between the first detection electrode and the first load module 101, ECGN represents a junction between the second detection electrode and the second load module 102, RL_OUT represents a junction between the third detection electrode and the third load module 103, and VSS represents a ground. In the first half period of a control clock, ECGP is connected to VDD through the first load module 101, ECGN is connected to VDD through the second load module 102, and RL_OUT is grounded through the third load module 103. In the second half period of the control clock, ECGP is grounded through the first load module 101, ECGN is grounded through the second load module 102, and RL_OUT is connected to VDD through the third load module 103. When the detection electrodes are all worn, voltages of ECGP and ECGN fluctuate slightly around VDD/2 if the polarizing voltage is relatively small, and VPH and VNH are both low levels. When LA is not worn and RA and RL are worn, the voltage of ECGP is cyclically pulled up to VDD and pulled down to the ground. A waveform of the voltage of ECGP (VECGP1) when LA is worn and a waveform of the voltage of ECGP (VECGP2) when LA is not worn are shown in FIG. 4. It can be seen from FIG. 4 that if the first comparator directly outputs VPH, the output also flips between high and low levels. In this embodiment, a corresponding sequential logic is set through the first logic processing module, so that when LA is not worn, the output is always a high level, and due to resistive voltage division, the ECGN voltage fluctuates between VDD/3 and 2VDD/3, to make VNH be a low level by using a proper threshold (that is, VTH_H). When RA is not worn, similar to the case in which LA is not worn, under an action of the second logic processing module, VPH is a low level, and VNH is a high level. When RL is not worn, or any two of LA, RA and RL are not worn, both the voltages of ECGP and ECGN are cyclically pulled up to VDD and pulled down to the ground, and VPH and VNH are both high levels after the output of the comparator meets a corresponding sequential logic.

Figure 5:
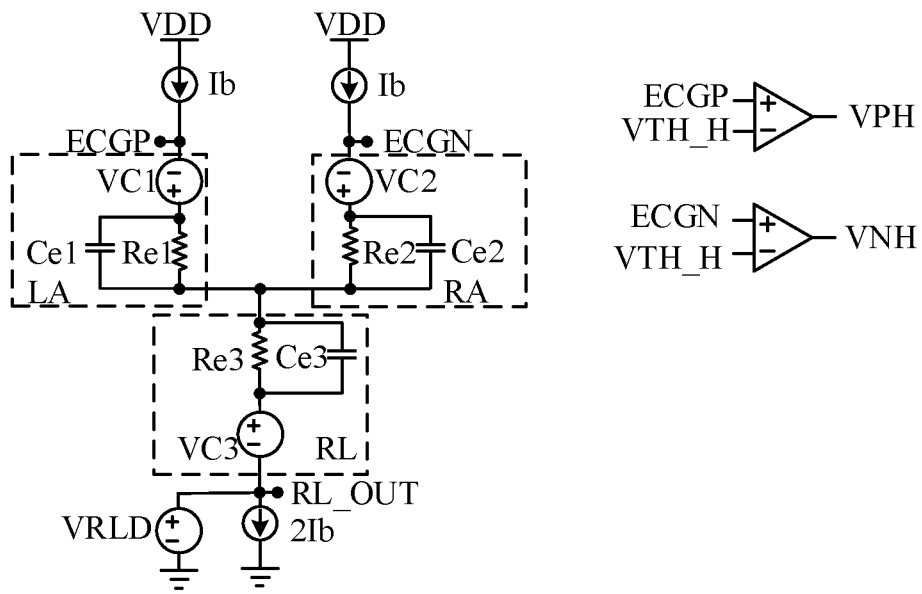
FIG. 5 is a schematic diagram of a circuit connection between a detection circuit and an ECG detection apparatus in an example C according to the first embodiment of the present disclosure.

In an example C, each of the first load module 101, the second load module 102, and the third load module 103 includes a first current source. The first electrical signal and the second electrical signal are high-level signals with a voltage value of VDD, and the third electrical signal is a low-level signal. A current output by the first current sources in the first load module 101 and the second load module 102 is Ib, and a current output by the first current source in the third load module 103 is 2Ib. Assuming that the first comparison reference signal and the second comparison reference signal are the same and both are VTH_H, where VDD/2<VTH_H<VDD. When the first detection electrode, the second detection electrode and the third detection electrode are all worn, a schematic circuit diagram of the detection circuit and the ECG detection apparatus is shown in FIG. 5 if a human body resistance is ignored. In FIG. 5, LA represents the left-hand electrode, RA represents the right-hand electrode, RL represents the RLD electrode, ECGP represents a junction between the first detection electrode and the first load module 101, ECGN represents a junction between the second detection electrode and the second load module 102, RL_OUT represents a junction between the third detection electrode and the third load module 103, and VRLD represents an output voltage of an RLD circuit. A correspondence between the wearing state of the detection electrode and the output of the comparator is shown in Table 1. A current output by the current source in the first load module 101 flows from VDD into ECGP, a current output by the current source in the second load module 102 flows from VDD into ECGN, and a current output by the current source in the third load module 103 flows into the ground. When the three detection electrodes are all worn, under an action of an RLD loop, voltages of ECGP and ECGN are biased at a common-mode voltage, which is about VDD/2, and therefore, VPH and VNH are both low levels. When LA falls off, the voltage of ECGP is pulled up to VDD by the current source, the voltage of ECGN is pulled to the ground under the action of the RLD loop, and therefore, VPH is a high level, and VNH is a low level. When RA falls off, similar to the case in which LA falls off, VPH is a low level, and VNH is a high level. When RL falls off or any two of LA, RA, and RL fall off, the voltages of ECGP and ECGN are both pulled up to VDD, and VPH and VNH are both high levels.

Figure 6:
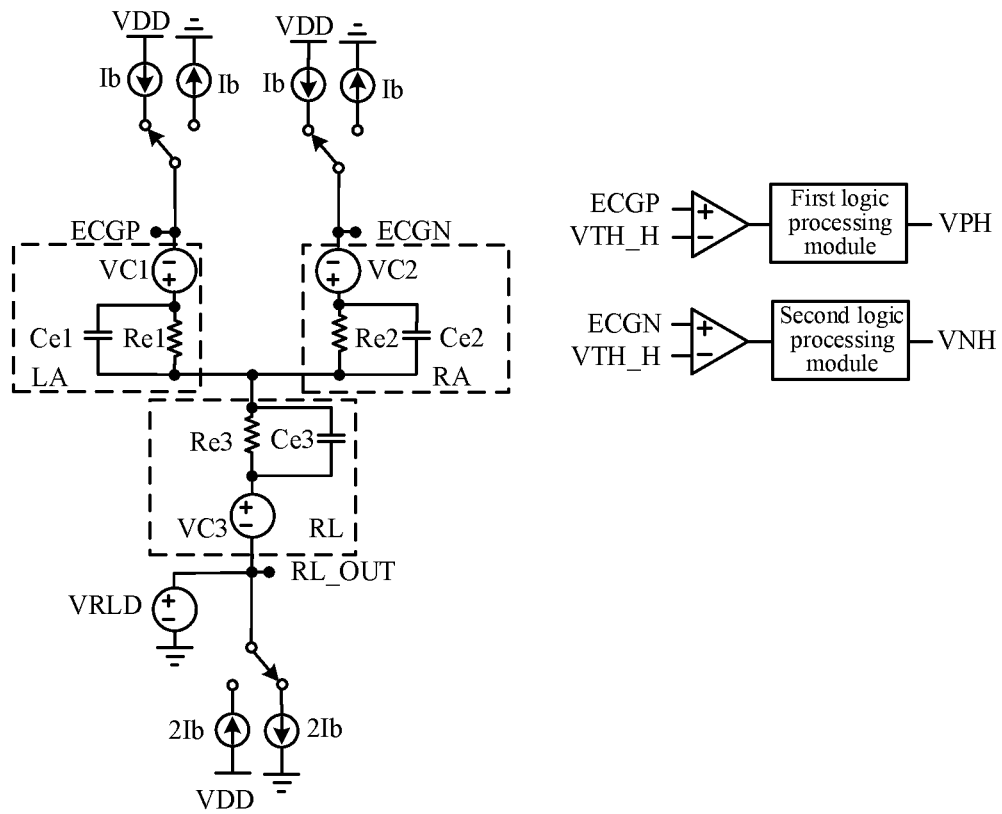
FIG. 6 is a schematic diagram of a circuit connection between a detection circuit and an ECG detection apparatus in an example D according to the first embodiment of the present disclosure.

In an example D, each of the first load module 101, the second load module 102, and the third load module 103 includes: a second current source, a third current source and a first change-over switch. A movable end of the first change-over switch serves as a second end of a load module, a first fixed end of the first change-over switch is connected to an end of the second current source, the other end of the second current source serves as a first end of the load module, a second fixed end of the first change-over switch is connected to an end of the third current source, and the other end of the third current source serves as a third end of the load module. The first electrical signal and the second electrical signal are high-level signals, and the third electrical signal is a low-level signal. Both a third end of the first load module 101 and a third end of the second load module 102 are connected to a low-level signal, and a third end of the third load module 103 is connected to a high-level signal. A voltage value of the high-level signal is VDD, currents output by the second current sources and the third current sources in the first load module 101 and the second load module 102 are Ib, and currents output by the second current source and the third current source in the third load module 103 are 2Ib. Assuming that the first comparison reference signal and the second comparison reference signal are the same and both are VTH_H, where a value range of VTH may be [2VDD/3, VDD]. When the first detection electrode, the second detection electrode and the third detection electrode are all worn, a schematic circuit diagram of the detection circuit and the ECG detection apparatus is shown in FIG. 6 if a human body resistance is ignored. In FIG. 6, LA represents the left-hand electrode, RA represents the right-hand electrode, RL represents the RLD electrode, ECGP represents a junction between the first detection electrode and the first load module 101, ECGN represents a junction between the second detection electrode and the second load module 102, RL_OUT represents a junction between the third detection electrode and the third load module 103, and VRLD represents an output voltage of an RLD circuit. In the first half period of the control clock, the correspondence between the wearing state of the detection electrode and the output of the comparator is shown in Table 1. Ib flows from VDD into ECGP and ECGN, and 2Ib flows into the ground. In the second half of the period, 2Ib flows from VDD to RL_OUT, and Ib flows from ECGP and ECGN to the ground. When the three detection electrodes are all worn, the voltages of ECGP and ECGN fluctuate slightly around the common-mode voltage, and VPH and VNH are both low levels. When LA falls off, the voltage of ECGP is cyclically pulled up to VDD or pulled down to the ground, the voltage of ECGN is also cyclically pulled down to the ground or pulled up to VDD under the action of the RLD loop. The corresponding sequential logic makes VPH constantly output as a high level and VNH constantly output as a low level when LA falls off. When RA falls off, similar to the case in which LA falls off, VPH is a low level, and VNH is a high level. When RL falls off or any two of LA, RA, and RL fall off, the voltages of ECGP and ECGN are both cyclically pulled up to VDD and pulled down to the ground, and VPH and VNH are both high levels after VPH and VNH meet the corresponding sequential logic.

It should be noted that a person skilled in the art can understand that in an actual application, other circuit forms can alternatively be designed, and the above examples are used merely for illustration.

Because ECG sampling is not started when the detection electrodes are not worn, resistance values of the first load module, the second load module, and the third load module do not need to be too large in this case. Therefore, the load module may have the circuit structures shown in the examples A and B. Resistance is used for detecting whether the detection electrode is worn, and no additional current bias is required, thereby greatly reducing a power consumption of the detection circuit. When the detection electrodes are all worn, ECG sampling is started, an input impedance of AFE is greater than 1 GΩ, and an impedance of the current source is much greater than the resistance under the same area. Therefore, the current source may be added to the detection circuit. That is, the detection circuits mentioned in the examples A and B may be used for performing wearing detection on the detection electrodes, and the detection circuits mentioned in the examples C and D can be used for performing falling-off detection on the detection electrodes.

In an embodiment, both a detection circuit corresponding to falling-off detection and a detection circuit corresponding to wearing detection are disposed. Specifically, based on FIG. 1, the detection circuit further includes: a fourth load module, a fifth load module, a sixth load module, a fourth detection module and a fifth detection module. A first end of the fourth load module is connected to a fourth electrical signal, a second end of the fourth load module is configured to connect to the first detection electrode, a first end of the fifth load module is connected to a fifth electrical signal, a second end of the fifth load module is configured to connect to the second detection electrode, a first end of the sixth load module is connected to a sixth electrical signal, and a second end of the sixth load module is configured to connect to the third detection electrode. An input end of the fourth detection module is connected to a junction between the fourth load module and the first detection electrode, an output end of the fourth detection module is connected to the obtaining module, an input end of the fifth detection module is connected to a junction between the fifth load module and the second detection electrode, and an output end of the fifth detection module is connected to the obtaining module. Levels of both the fourth electrical signal and the fifth electrical signal are opposite to a level of the sixth electrical signal.

In a first case, each of the first load module, the second load module, and the third load module includes the first resistor unit, and each of the fourth load module, the fifth load module and the sixth load module includes: a fourth current source and a fourth switch, where a first end of the fourth current source serves as a first end of a load module corresponding to the fourth current source, a second end of the fourth current source is connected to a first end of the fourth switch, and a second end of the fourth switch serves as a second end of the load module corresponding to the fourth current source.

In a second case, each of the first load module, the second load module, and the third load module includes: the second resistor unit and the first change-over switch, and each of the fourth load module, the fifth load module and the sixth load module includes: a fifth current source, a sixth current source, a second change-over switch and a fourth switch, where a movable end of the second change-over switch is connected to a first end of the fourth switch, a second end of the fourth switch serves as a second end of a load module corresponding to the second change-over switch, a first fixed end of the second change-over switch is connected to an end of the fifth current source, the other end of the fifth current source serves as a first end of the load module corresponding to the second change-over switch, a second fixed end of the second change-over switch is connected to an end of the sixth current source, and the other end of the sixth current source serves as a third end of the load module corresponding to the second change-over switch. The fourth electrical signal and the fifth electrical signal are high-level signals, and the sixth electrical signal is a low-level signal. Both a third end of the fourth load module and a third end of the fifth load module are connected to a low-level signal, and a third end of the sixth load module is connected to a high-level signal.

In the above cases, the obtaining module is further configured to: turn on, after determining that the ECG detection apparatus is in a sleep state, the first switch, the second switch, and the third switch, turn off the fourth switch in the fourth load module, the fifth load module, and the sixth load module, and obtain the electrical signal output by the first detection module and the electrical signal output by the second detection module to determine whether the first detection electrode, the second detection electrode, and the third detection electrode are worn; and turn off, after determining that the ECG detection apparatus is in a working state, the first switch, the second switch, and the third switch, turn off the fourth switch in the fourth load module, the fifth load module, and the sixth load module, and obtain an electrical signal output by the fourth detection module and an electrical signal output by the fifth detection module to determine whether the first detection electrode, the second detection electrode, and the third detection electrode fall off. For operation principles of the circuit including the fourth load module, the fifth load module, the sixth load module, the fourth detection module and the fifth detection module, refer to the related descriptions of the above examples C and D.

It should be noted that in this embodiment, the sleep state of the ECG detection apparatus is a state in which the three detection electrodes of the ECG detection apparatus are not worn, and ECG testing is performed. The working state is a state in which the three detection electrodes are worn, and ECG testing starts or is about to start.

In an embodiment, the obtaining module may determine a current state of the ECG detection apparatus according to a received instruction. For example, after a wearing detection instruction or a detection stop instruction is received, it is considered that the ECG detection apparatus is in the sleep state, and after a detection start instruction is received, it is considered that the ECG detection apparatus is in the working state.

In an example, a circuit including the first load module, the second load module, the third load module, the first detection module and the second detection module may refer to FIG. 2. A circuit including the fourth load module, the fifth load module, the sixth load module, the fourth detection module and the fifth detection module may refer to FIG. 5.

In another example, a circuit including the first load module, the second load module, the third load module, the first detection module and the second detection module may refer to FIG. 3. A circuit including the fourth load module, the fifth load module, the sixth load module, the fourth detection module and the fifth detection module may refer to FIG. 6.

Compared with existing technologies, when the three detection electrodes are all worn, there is an electrical conduction path between the first load module and the third load module, and there is an electrical conduction path between the second load module and the third load module in the embodiments of the present disclosure. When one or more of the three detection electrodes are not worn, electrical signals detected by the first detection module and the second detection module are different. Therefore, a wearing state or a falling-off state of the first detection electrode, the second detection electrode and the third detection electrode can be determined according to a signal received by the obtaining module, so that a case in which the first detection electrode, the second detection electrode and the third detection electrode are not worn normally can be found in time.

A second embodiment of the present disclosure relates to a detection circuit. The detection circuit mentioned in this embodiment is basically the same as the detection circuit mentioned in the first embodiment. A main difference is that in this embodiment, the detection circuit also includes a third detection module.

Figure 7:
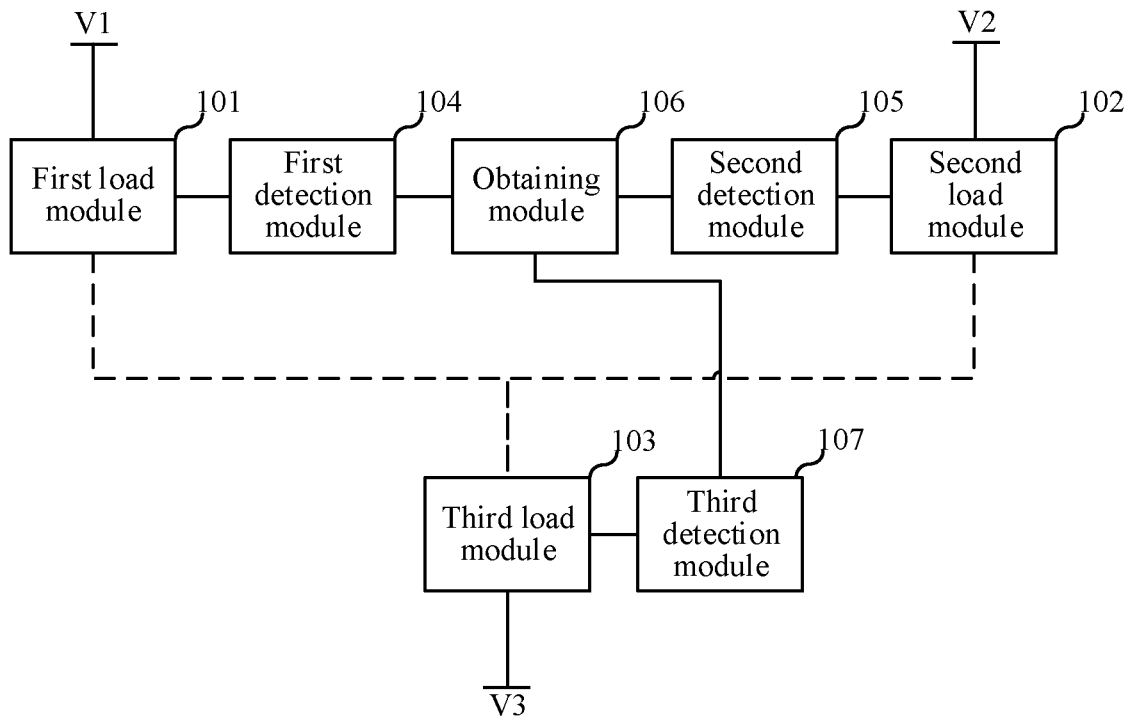
FIG. 7 is a schematic structural diagram of a detection circuit according to a second embodiment of the present disclosure.

Specifically, as shown in FIG. 7, the detection circuit further includes a third detection module 107, an input end of the third detection module 107 is connected to a junction between the third detection electrode and the third load module 103, and an output end of the third detection module 107 is connected to the obtaining module 106. The obtaining module 106 is configured to obtain the electrical signal output by the first detection module 104, the electrical signal output by the second detection module 105, and an electrical signal output by the third detection module 107, to determine the wearing state or the falling-off state of the first detection electrode, the second detection electrode and the third detection electrode.

Figure 8:
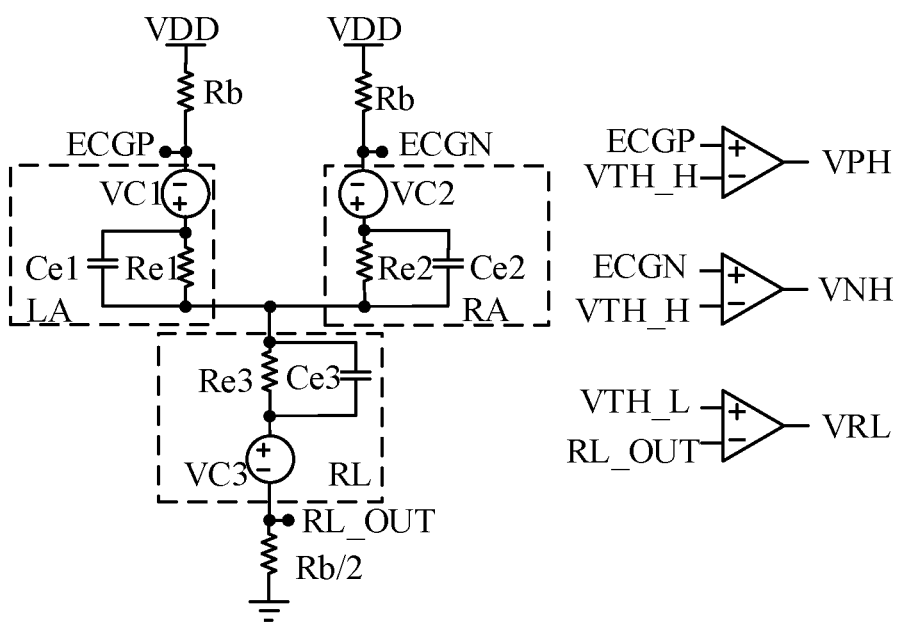
FIG. 8 is a schematic diagram of a circuit connection between the detection circuit and an ECG detection apparatus according to the second embodiment of the present disclosure.

In an example, the third detection module 107 includes a third comparator, a first input end of the third comparator serves as the input end of the third detection module 107, a second input end of the third comparator is connected to a third comparison reference signal, and an output end of the third comparator serves as the output end of the third detection module 107. Specifically, using the detection circuit shown in the example A of the first embodiment as an example, after the third detection module 107 is added, a schematic circuit diagram of the detection circuit and the ECG detection apparatus is shown in FIG. 8. A voltage at the junction between the third detection electrode and the third load module 103 is detected. When RL falls off, the voltage at the junction (RL_OUT) between the third detection electrode and the third load module 103 is 0 V under any polarizing voltage. The third comparator outputs a high level, thereby improving a success rate of the wearing/falling-off detection under extreme conditions.

It should be noted that a person skilled in the art can understand that in an actual application, another device or another circuit form may be selected as the third detection module 107. A specific circuit of the third detection module is not limited in this embodiment.

Compared with existing technologies, a third detection module 103 is added to detect the voltage at the junction between the third detection electrode and the third load module 103 in this embodiment, thereby improving a detection success rate of the detection circuit under extreme conditions.

A third embodiment of the present disclosure further relates to an ECG detection apparatus, including: a first detection electrode, a second detection electrode, a third detection electrode and the detection circuit mentioned in the first embodiment or the second embodiment.

In an embodiment, the ECG detection apparatus may include two detection circuits. One detection circuit, as shown in FIG. 2 or 3, is configured to perform wearing detection, and the other detection circuit, as shown in FIG. 5 or 6 is configured to perform falling-off detection.

A fourth embodiment of the present disclosure further relates to a wearable device, including: a first detection electrode, a second detection electrode, a third detection electrode and the detection circuit mentioned in the first embodiment or the second embodiment.

A person of ordinary skill in the art can understand that the above embodiments are specific examples for implementing the present disclosure, and in an actual application, various changes can be made in terms of forms and details without departing from the spirit and scope of the present disclosure.

What is claimed is:

1. A detection circuit, applicable to an electrocardiogram (ECG) detection apparatus, the ECG detection apparatus comprising a first detection electrode, a second detection electrode and a third detection electrode, the detection circuit comprising a first load module, a second load module, a third load module, a first detection module, a second detection module and an obtaining module; wherein, a first end of the first load module is configured to be coupled to a first voltage level, a first end of the second load module is configured to be coupled to a second voltage level, a second end of the first load module is configured to connect to the first detection electrode, a second end of the second load module is configured to connect to the second detection electrode, a first end of the third load module is configured to be coupled to a third voltage level, and a second end of the third load module is configured to connect to the third detection electrode;

an input end of the first detection module is connected to a junction of the first detection electrode and the first load module, an output end of the first detection module is connected to the obtaining module, an input end of the second detection module is connected to a junction of the second detection electrode and the second load module, an output end of the second detection module is connected to the obtaining module, and each of the first voltage level and the second voltage level is different from the third voltage level; and the obtaining module is configured to at least obtain an electrical signal output by the first detection module and an electrical signal output by the second detection module, to determine a wearing state or a non-wearing state of the first detection electrode, the second detection electrode and the third detection electrode.

2. The detection circuit according to claim 1, wherein the first detection module comprises a first comparator, a first input end of the first comparator serves as the input end of the first detection module, a second input end of the first comparator is connected to a first comparison reference signal, and an output end of the first comparator serves as the output end of the first detection module.

3. The detection circuit according to claim 1, wherein the second detection module comprises a second comparator, a first input end of the second comparator serves as the input end of the second detection module, a second input end of the second comparator is connected to a second comparison reference signal, and an output end of the second comparator serves as the output end of the second detection module.

4. The detection circuit according to claim 1, wherein the obtaining module is further configured to: determine the wearing state or the non-wearing state of the first detection electrode, the second detection electrode and the third detection electrode at least according to a level of the electrical signal output by the first detection module and a level of the electrical signal output by the second detection module.

5. The detection circuit according to claim 1, wherein a resistance value of the first load module is the same as a resistance value of the second load module.

6. The detection circuit according to claim 1, wherein the detection circuit further comprises a third detection module, an input end of the third detection module is connected to a junction of the third detection electrode and the third load module, and an output end of the third detection module is connected to the obtaining module; and the obtaining module is configured to obtain the electrical signal output by the first detection module, the electrical signal output by the second detection module, and an electrical signal output by the third detection module, to determine the wearing state or the non-wearing state of the first detection electrode, the second detection electrode and the third detection electrode.

7. The detection circuit according to claim 6, wherein the third detection module comprises a third comparator, a first input end of the third comparator serves as the input end of the third detection module, a second input end of the third comparator is connected to a third comparison reference signal, and an output end of the third comparator serves as the output end of the third detection module.

8. The detection circuit according to claim 1, wherein each of the first load module, the second load module, and the third load module comprises: a first resistor unit or a first current source.

9. The detection circuit according to claim 8, wherein the detection circuit further comprises a first switch, a second switch and a third switch, the second end of the first load module is connected to the first detection electrode through the first switch, the second end of the second load module is connected to the second detection electrode through the second switch, and the second end of the third load module is connected to the third detection electrode through the third switch.

10. The detection circuit according to claim 9, wherein the detection circuit further comprises a fourth load module, a fifth load module, a sixth load module, a fourth detection module and a fifth detection module, a first end of the fourth load module is configured to be coupled to a fourth voltage level, a second end of the fourth load module is configured to connect to the first detection electrode, a first end of the fifth load module is configured to be coupled to a fifth voltage level, a second end of the fifth load module is configured to connect to the second detection electrode, a first end of the sixth load module is configured to be coupled to a sixth voltage level, and a second end of the sixth load module is configured to connect to the third detection electrode, an input end of the fourth detection module is connected to a junction of the fourth load module and the first detection electrode, an output end of the fourth detection module is connected to the obtaining module, an input end of the fifth detection module is connected to a junction of the fifth load module and the second detection electrode, an output end of the fifth detection module is connected to the obtaining module, and each of the fourth voltage level and the fifth voltage level is different from the sixth voltage level;

each of the first load module, the second load module, and the third load module comprises a first resistor unit, and each of the fourth load module, the fifth load module and the sixth load module comprises: a fourth current source and a fourth switch, wherein a first end of the fourth current source serves as a first end of a load module corresponding to the fourth current source, a second end of the fourth current source is connected to a first end of the fourth switch, and a second end of the fourth switch serves as a second end of the load module corresponding to the fourth current source; or each of the first load module, the second load module, and the third load module comprises: the second resistor unit and the first change-over switch, and each of the fourth load module, the fifth load module and the sixth load module comprises: a fifth current source, a sixth current source, a second change-over switch and a fourth switch, wherein a movable end of the second change-over switch is connected to a first end of the fourth switch, a second end of the fourth switch serves as a second end of a load module corresponding to the second change-over switch, a first fixed end of the second change-over switch is connected to an end of the fifth current source, the other end of the fifth current source serves as a first end of the load module corresponding to the second change-over switch, a second fixed end of the second change-over switch is connected to an end of the sixth current source, and the other end of the sixth current source serves as a third end of the load module corresponding to the second change-over switch;

the fourth voltage level and the fifth voltage level are each at a higher level than the sixth voltage level, both a third end of the fourth load module and a third end of the fifth load module are configured to be coupled connected to a voltage level lower than the fourth or fifth voltage level, and a third end of the sixth load module is configured to be coupled to a voltage level higher than the sixth voltage level; and the obtaining module is further configured to: turn on, after determining the ECG detection apparatus is in a sleep state, the first switch, the second switch, and the third switch, turn off the fourth switch in the fourth load module, the fifth load module, and the sixth load module, and obtain the electrical signal output by the first detection module and the electrical signal output by the second detection module to determine whether the first detection electrode, the second detection electrode, and the third detection electrode are worn; and turn off, after determining that the ECG detection apparatus is in a working state, the first switch, the second switch, and the third switch, turn on the fourth switch in the fourth load module, the fifth load module, and the sixth load module, and obtain an electrical signal output by the fourth detection module and an electrical signal output by the fifth detection module to determine whether the first detection electrode, the second detection electrode, and the third detection electrode fall off.

11. The detection circuit according to claim 1, wherein each of the first load module, the second load module, and the third load module comprises: a second resistor unit and a first change-over switch, a first fixed end of the first change-over switch serves as a first end of a load module corresponding to the first change-over switch, a second fixed end of the first change-over switch serves as a third end of the load module corresponding to the first change-over switch, a movable end of the first change-over switch is connected to a first end of the second resistor unit, and a second end of the second resistor unit serves as a second end of the load module corresponding to the first change-over switch; or,
    each of the first load module, the second load module, and the third load module comprises: a second current source, a third current source and a first change-over switch, a movable end of the first change-over switch serves as a second end of a load module corresponding to the first change-over switch, a first fixed end of the first change-over switch is connected to an end of the second current source, the other end of the second current source serves as a first end of the load module corresponding to the first change-over switch, a second fixed end of the first change-over switch is connected to an end of the third current source, and the other end of the third current source serves as a third end of the load module corresponding to the first change-over switch;

wherein the first voltage level and the second voltage level are each at a higher level than the third voltage level, and both a third end of the first load module and a third end of the second load module are configured to be coupled to a voltage level lower than the first or second voltage level, and a third end of the third load module is configured to be coupled to a voltage level higher than the third voltage level.

12. The detection circuit according to claim 11, wherein the obtaining module is further configured to: control, after determining that the ECG detection apparatus is in a direct current (DC) working mode, the movable end of the first change-over switch to connect to the first fixed end of the first change-over switch; and control, after determining that the ECG detection apparatus is in an alternating current (AC) working mode, the movable end of the first change-over switch to periodically switch between being connected to the first fixed end of the first change-over switch and connected to the second fixed end of the first change-over switch.

13. The detection circuit according to claim 11, wherein the detection circuit further comprises a first logic processing module and a second logic processing module, the output end of the first detection module is connected to the obtaining module through the first logic processing module, and the output end of the second detection module is connected to the obtaining module through the second logic processing module;

the first logic processing module is configured to output an electrical signal with a first level when an electrical signal output by the first detection module meets a preset first sequential logic, and output an electrical signal with a second level when an electrical signal output by the first detection module does not meet the preset first sequential logic, the first level being opposite to the second level; and the second logic processing module is configured to output an electrical signal with a third level when an electrical signal output by the second detection module meets a preset second sequential logic, and output an electrical signal with a fourth level when an electrical signal output by the second detection module does not meet the preset second sequential logic, the third level being opposite to the fourth level.

14. The detection circuit according to claim 11, wherein the detection circuit further comprises a first switch, a second switch and a third switch, the second end of the first load module is connected to the first detection electrode through the first switch, the second end of the second load module is connected to the second detection electrode through the second switch, and the second end of the third load module is connected to the third detection electrode through the third switch.

15. The detection circuit according to claim 1, wherein the first end of the first load module and the first end of the third load module are coupled, respectively, to two opposite output ends of a power supply, and the first end of the second load module is coupled to a same output end of the power supply as the first end of the first load module.

16. The detection circuit according to claim 1, wherein a voltage at a junction between the first detection electrode and the first load module is pulled up to the first voltage level when the first detection electrode is in the non-wearing state while the second detection electrode and the third detection electrode are each in the wearing state.

17. The detection circuit according to claim 1, wherein a voltage at a junction between the first detection electrode and the first load module is pulled up to the first voltage level, and a voltage at a junction between the second detection electrode and the second load module is pulled up to the second voltage level, when the third detection electrode, or any two of the first detection electrode, the second detection electrode, and the third detection electrode, are each in the non-wearing state.

18. An electrocardiogram (ECG) detection apparatus, comprising a first detection electrode, a second detection electrode, a third detection electrode and a detection circuit, the detection circuit comprising a first load module, a second load module, a third load module, a first detection module, a second detection module and an obtaining module; wherein, a first end of the first load module is configured to be coupled to a first voltage level, a first end of the second load module is configured to be coupled to a second voltage level, a second end of the first load module is configured to connect to the first detection electrode, a second end of the second load module is configured to connect to the second detection electrode, a first end of the third load module is configured to be coupled to a third voltage level, and a second end of the third load module is configured to connect to the third detection electrode;

an input end of the first detection module is connected to a junction of the first detection electrode and the first load module, an output end of the first detection module is connected to the obtaining module, an input end of the second detection module is connected to a junction of the second detection electrode and the second load module, an output end of the second detection module is connected to the obtaining module, and each of the first voltage level and the second voltage level is different from the third voltage level; and the obtaining module is configured to at least obtain an electrical signal output by the first detection module and an electrical signal output by the second detection module, to determine a wearing state or a non-wearing state of the first detection electrode, the second detection electrode and the third detection electrode.

19. A wearable device, comprising a first detection electrode, a second detection electrode, a third detection electrode and a detection circuit, the detection circuit comprising a first load module, a second load module, a third load module, a first detection module, a second detection module and an obtaining module; wherein, a first end of the first load module is configured to be coupled to a first voltage level, a first end of the second load module is configured to be coupled to a second voltage level, a second end of the first load module is configured to connect to the first detection electrode, a second end of the second load module is configured to connect to the second detection electrode, a first end of the third load module is configured to be coupled to a third voltage level, and a second end of the third load module is configured to connect to the third detection electrode;

an input end of the first detection module is connected to a junction of the first detection electrode and the first load module, an output end of the first detection module is connected to the obtaining module, an input end of the second detection module is connected to a junction of the second detection electrode and the second load module, an output end of the second detection module is connected to the obtaining module, and each of the first voltage level and the second voltage level is different from the third voltage level; and the obtaining module is configured to at least obtain an electrical signal output by the first detection module and an electrical signal output by the second detection module, to determine a wearing state or a non-wearing state of the first detection electrode, the second detection electrode and the third detection electrode.

* * * * *